(12) United States Patent
Bordeaux et al.

(10) Patent No.: US 12,383,315 B2
(45) Date of Patent: Aug. 12, 2025

(54) ORTHOPEDIC IMPLANT ALTERING APPARATUS AND ASSOCIATED METHOD OF USE

(71) Applicant: GLOBUS MEDICAL, INC., Audubon, PA (US)

(72) Inventors: Jean-Noel Bordeaux, West Chester, PA (US); Madeline Mitchell, Norristown, PA (US); Anna Kedzierska, Philadelphia, PA (US); Rebecca Gray, Spring City, PA (US)

(73) Assignee: Globus Medical, Inc., Audubon, PA (US)

( * ) Notice: Subject to any disclaimer, the term of this patent is extended or adjusted under 35 U.S.C. 154(b) by 264 days.

(21) Appl. No.: 18/326,113

(22) Filed: May 31, 2023

(65) Prior Publication Data

US 2024/0398447 A1 Dec. 5, 2024

(51) Int. Cl.
*A61B 17/72* (2006.01)
*A61F 2/46* (2006.01)

(52) U.S. Cl.
CPC ............... *A61B 17/72* (2013.01); *A61F 2/46* (2013.01); *A61F 2220/0025* (2013.01); *A61F 2310/00023* (2013.01)

(58) Field of Classification Search
CPC .................................. A61F 2/46; A61B 17/72
See application file for complete search history.

(56) References Cited

U.S. PATENT DOCUMENTS

| | | | | |
|---|---|---|---|---|
| 1,089,362 | A * | 3/1914 | Hannifin | B23B 31/16083 279/117 |
| 4,565,192 | A * | 1/1986 | Shapiro | A61B 17/1604 606/88 |
| 4,633,862 | A * | 1/1987 | Petersen | A61B 17/2812 606/88 |
| 4,995,875 | A * | 2/1991 | Coes | A61B 17/02 600/210 |
| 6,644,087 | B1 | 11/2003 | Ralph et al. | |
| 7,566,335 | B1 * | 7/2009 | Scott | A61B 17/158 606/88 |

(Continued)

FOREIGN PATENT DOCUMENTS

| | | |
|---|---|---|
| CN | 209332241 U | 12/2015 |
| CN | 204839715 U | 9/2019 |
| CN | 210784637 U | 6/2020 |

(Continued)

*Primary Examiner* — Christian A Sevilla

(57) ABSTRACT

An apparatus and method for orthopedic implant altering include a first member, having a rotatable slot, which is connected to a first lever that is supported and rotatable in a support member attached to a screw mechanism that connects to an anvil that translates rotational force from the first lever into an axial force to move the anvil. There are two or more upright posts attached to a movable table, where an orthopedic implant positioned between the anvil and the plurality of upright posts can be altered (cut or bent) by applying force through axial movement of the anvil. There is a second lever in a second member that is movable along a base plate and having a fixed slot and securing mechanism, wherein the orthopedic implant can also be selectively placed between the first slot and the second slot to apply an axial twist to the orthopedic implant.

20 Claims, 12 Drawing Sheets

(56) References Cited

U.S. PATENT DOCUMENTS

2013/0211410 A1* 8/2013 Landes .............. A61B 17/1767
  606/88
2021/0346074 A1 11/2021 Beyer

FOREIGN PATENT DOCUMENTS

| | | |
|---|---|---|
| CN | 210843405 U | 6/2020 |
| CN | 211325521 U | 8/2020 |
| CN | 212821906 U | 3/2021 |
| CN | 214160969 U | 9/2021 |
| CN | 214639380 U | 11/2021 |
| CN | 216394228 U | 4/2022 |
| CN | 218009927 U | 12/2022 |
| EP | 2903545 | 8/2015 |
| WO | 2014055081 A1 | 4/2014 |

* cited by examiner

ORTHOPEDIC IMPLANT ALTERING APPARATUS AND ASSOCIATED METHOD OF USE

TECHNICAL FIELD

The present disclosure generally relates to an apparatus and method to bend, shape, or cut an orthopedic implant, e.g., a bone plate. More particularly, but not exclusively, the present disclosure relates to an orthopedic implant altering system that not only achieves a desired shape or cut with minimum force but also can provide an axial twist.

BACKGROUND

The background description provided herein gives context for the present disclosure. Work of the presently named inventors, as well as aspects of the description that may not otherwise qualify as prior art at the time of filing, are neither expressly nor impliedly admitted as prior art.

Orthopedic implants, especially bone plates, often require adjustment to their original shape during the implantation surgical procedure. First, the orthopedic implant will be adjusted to match a particular anatomy or fracture site. Then, the reshaping of the orthopedic implant is performed manually during the surgery, either by the surgeon or medical support personnel. Depending on the type of orthopedic implant, it may be shaped using manual "bending irons" or with a table-top altering device.

The current table-top altering devices typically use a lever mechanism to amplify the force applied by the user. Unfortunately, the mechanism of the lever-type benders results in forces that are inconsistent throughout the procedure, potentially creating errors in the desired shape of the orthopedic implant. Moreover, a second operator may be needed to provide stability due to a lack of counter torque built into the device. The lever-type benders also can cause a sudden deformation of the bone plate. In addition, the forces required to utilize the lever can be such that they preclude use by smaller individuals and remain challenging when altering the largest implants. Furthermore, due to their design, these devices are large and heavy, and provide limited options for cleaning and sterilization.

In addition to planar bending, it is often necessary to twist the orthopedic implants axially to achieve the desired shape. There is currently no known table-top orthopedic implant bender that provides a mechanism to create an axial twist.

Thus, there exists a need in the art for an apparatus that can easily bend orthopedic implants, e.g., bone plates, with minimal force and also provide an axial twist.

SUMMARY

The following objects, features, advantages, aspects, and/or embodiments, are not exhaustive and do not limit the overall disclosure. No single embodiment needs to provide each and every object, feature, or advantage. Any of the objects, features, advantages, aspects, and/or embodiments disclosed herein can be integrated with one another, either in full or in part.

It is a primary object, feature, and/or advantage of the present disclosure to improve on or overcome the deficiencies in the art.

An advantage of the present invention is that it produces a constant force to bend an orthopedic implant, e.g., bone plate, permitting more predictable results.

Another advantage of the present invention is that there is a screw mechanism that provides a greater mechanical advantage such that less force is required to bend an orthopedic implant, e.g., bone plate, compared to other orthopedic implant altering devices.

Still another advantage of this present invention is a mechanism to twist an orthopedic implant, e.g., bone plate, axially that is not available in other types of table-top devices used for altering orthopedic implants.

Yet another advantage of this present invention is a second lever that permits the application of a counter-torque, preventing movement along the table, and removing the necessity of a second operator.

Still yet another advantage of this present invention is an orthopedic implant altering apparatus that has a smaller footprint than current devices and can include a collapsible hand lever that permits the orthopedic implant altering apparatus to fit into standard sterilization containers with minimal disassembly.

A further advantage of the present invention is that the orthopedic implant altering apparatus facilitates disassembly, cleaning, and repair.

A still yet further advantage of the present invention is fully interchangeable bending and cutting components to selectively alter a spectrum of orthopedic implants to address a patient's physical condition.

It is an aspect of the present invention involving an orthopedic implant altering apparatus that includes a base plate having a support member, a first lever, a first member that is connected to the first lever that is supported and rotatable in the support member, a screw mechanism, having a first end portion and a second end portion, wherein the first end portion is connected to the first member, an anvil, having a first end portion and a second end portion, wherein the first end portion is connected to the second end portion of the screw mechanism to translate rotational force from the first lever into an axial force, a movable table, and a plurality of upright posts attached to the movable table, wherein an orthopedic implant positioned between the anvil and the plurality of upright posts can be altered by applying force through axial movement of the anvil.

It is another aspect of the present invention that includes an orthopedic implant altering apparatus with a screw mechanism that includes a first end portion attached to the first member and the second end portion having a threaded shaft, wherein the anvil includes an anvil base member having a first end portion with recessed threads that interact with the threaded shaft of the screw mechanism and a second end portion of the anvil base member that can selectively connect to an anvil contact member.

Another feature of the present invention of an orthopedic implant altering apparatus is that an orthopedic implant is selected from the group consisting of a bone plate, intramedullary nails, pins, and rods.

It is still another aspect of the present invention of an orthopedic implant altering apparatus is that the base plate can be located in a vertical plane.

Yet another aspect of the present invention of an orthopedic implant altering apparatus involves a second lever attached to a second member having a fixed slot, wherein the second member is adjustably movable along the base plate, and the first member also includes a rotatable slot that is rotatable by the first lever; wherein the orthopedic implant can be selectively placed between the slot of the first member and the slot of the second member with the first lever being able to rotate the slot of the first member and apply an axial twist to the orthopedic implant.

Still, yet another feature of the present invention of an orthopedic implant altering apparatus involves the second member having a sliding mechanism that engages the base plate allowing movement of the second member so that the distance between the rotatable slot of the first member and the fixed slot of the second member can secure the orthopedic implant and the second member also includes an adjustable securing mechanism for fixedly securing the orthopedic implant within the fixed slot of the second member.

Another feature of the present invention of an orthopedic implant altering apparatus involves a movable table that has at least one protruding flange member that engages an underside of the base plate.

Still another aspect of the present invention of an orthopedic implant altering apparatus includes each upright post of the plurality of upright posts can vary based on the orthopedic implant and desired alteration and is selectively interchangeable with the movable table.

A further feature of the present invention of an orthopedic implant altering apparatus includes each upright post of the plurality of upright posts having at least one prong that is selectively engageable with at least one slot in the movable table.

Yet another feature of the method of the present invention of an orthopedic implant altering apparatus includes a threaded opening within the movable table and an adjustment knob inserted within the threaded opening to be able to manually adjust the position of the plurality of upright posts in relation to the anvil contact member so that the orthopedic implant is securely positioned in between.

It is still another feature of the present invention of an orthopedic implant altering apparatus includes a second lever, when gripped can counteract the torque produced by the first lever in either a bending or twisting operation to secure the base plate's position.

In still yet another aspect of the present invention of an orthopedic implant altering apparatus includes an anvil contact member that can be in the form of a group consisting of a medium bender, a narrow bender, a broad bender, a rod bender, and a rod cutter and is selectively interchangeable with the anvil base member depending on a patient and associated medical condition.

It is yet another aspect of the present invention of an orthopedic implant altering apparatus that includes an anvil base member that having an opening, and an anvil contact member includes a protruding member that is securely received within the opening of the anvil base member.

Still, yet another feature of the system of the present invention of an orthopedic implant altering apparatus includes a first lever is located underneath a covered member and the second lever is attached to a track that is received underneath the base plate and is adjustably movable.

Another feature of the present invention is an orthopedic implant altering apparatus that includes a base plate having a support member, a first lever, a first member that is connected to the first lever that is supported and rotatable in the support member and having a rotatable slot, a threaded shaft, having a first end portion and a second end portion, wherein the first end portion is connected to the first member, an anvil base member, having a first end portion and a second end portion, wherein the first end portion is a threaded portion and interacts with the second end portion of the threaded shaft to translate rotational force from the first lever into an axial force and the second end portion of the anvil base member includes an opening, an anvil contact member attached to the anvil base member through an attachment member that is received by the opening of the anvil base member, a plurality of upright posts attached to a movable table; wherein an orthopedic implant positioned between the anvil contact member and the plurality of upright posts can be altered by applying force through axial movement of the anvil contact member, and a second lever attached to a second member having a fixed slot that is adjustably movable along the base plate and an adjustable securing mechanism for fixedly securing the orthopedic implant in the fixed slot, wherein the orthopedic implant can be selectively placed between the rotatable slot of the first member and the fixed slot of the second member, with the first lever being able to apply an axial twist to the orthopedic implant.

It is an aspect of the present invention of an orthopedic implant altering apparatus that an orthopedic implant is selected from the group consisting of bone plates, intramedullary nails, pins, and rods.

A further aspect of the present invention of an orthopedic implant altering apparatus includes an anvil contact member that is selectively attachable to the anvil base member and the upright posts are selectively attachable to the movable table where both the anvil contact member and upright posts can vary depending on the orthopedic implant and medical condition of the patient.

Still yet an additional aspect of the present invention of an orthopedic implant altering apparatus includes a movable table that includes a protruding flange member that engages the underside of the base plate, and there is a threaded opening within the movable table and an adjustment knob inserted within the threaded opening to be able to manually adjust the position of the plurality of upright posts in relation to the anvil contact member so that an orthopedic implant can be securely positioned in between the anvil contact member and the upright posts.

Another aspect of the present invention includes a method for altering orthopedic implants that includes inserting an orthopedic implant securely between an anvil contact member and a plurality of movable upright posts, and rotating a first lever having a first member that is supported and rotatable in a support member that is attached to a base plate, wherein a first end portion of the first member is connected to a screw mechanism that is then connected to an anvil base member, wherein the rotational force of the first lever is converted to axial movement to alter the orthopedic implant due to the force caused by the moving anvil contact member against the orthopedic member that is pressed against the plurality of upright posts on a movable table.

Still, another feature of the method of the present invention for altering orthopedic implants includes placing and securing an orthopedic implant in a fixed slot in a second member and a rotatable slot in the first member and rotating the first lever to apply an axial twist to the orthopedic implant.

These and/or other objects, features, advantages, aspects, and/or embodiments will become apparent to those skilled in the art after reviewing the following brief and detailed descriptions of the drawings. The present disclosure encompasses (a) combinations of disclosed aspects and/or embodiments and/or (b) reasonable modifications not shown or described.

BRIEF DESCRIPTION OF THE DRAWINGS

Several embodiments in which the present disclosure can be practiced are illustrated and described in detail, wherein like reference characters represent like components throughout the several views. The drawings are presented for exemplary purposes and may not be to scale unless otherwise indicated.

An artisan of ordinary skill in the art need not view, within isolated figure(s), the near infinite distinct combinations of features described in the following detailed description to facilitate an understanding of the present disclosure.

DETAILED DESCRIPTION

The present disclosure is not to be limited to that described herein. Mechanical, electrical, chemical, procedural, and/or other changes can be made without departing from the spirit and scope of the present disclosure. No features shown or described are essential to permit the basic operation of the present disclosure unless otherwise indicated.

Figure 1:
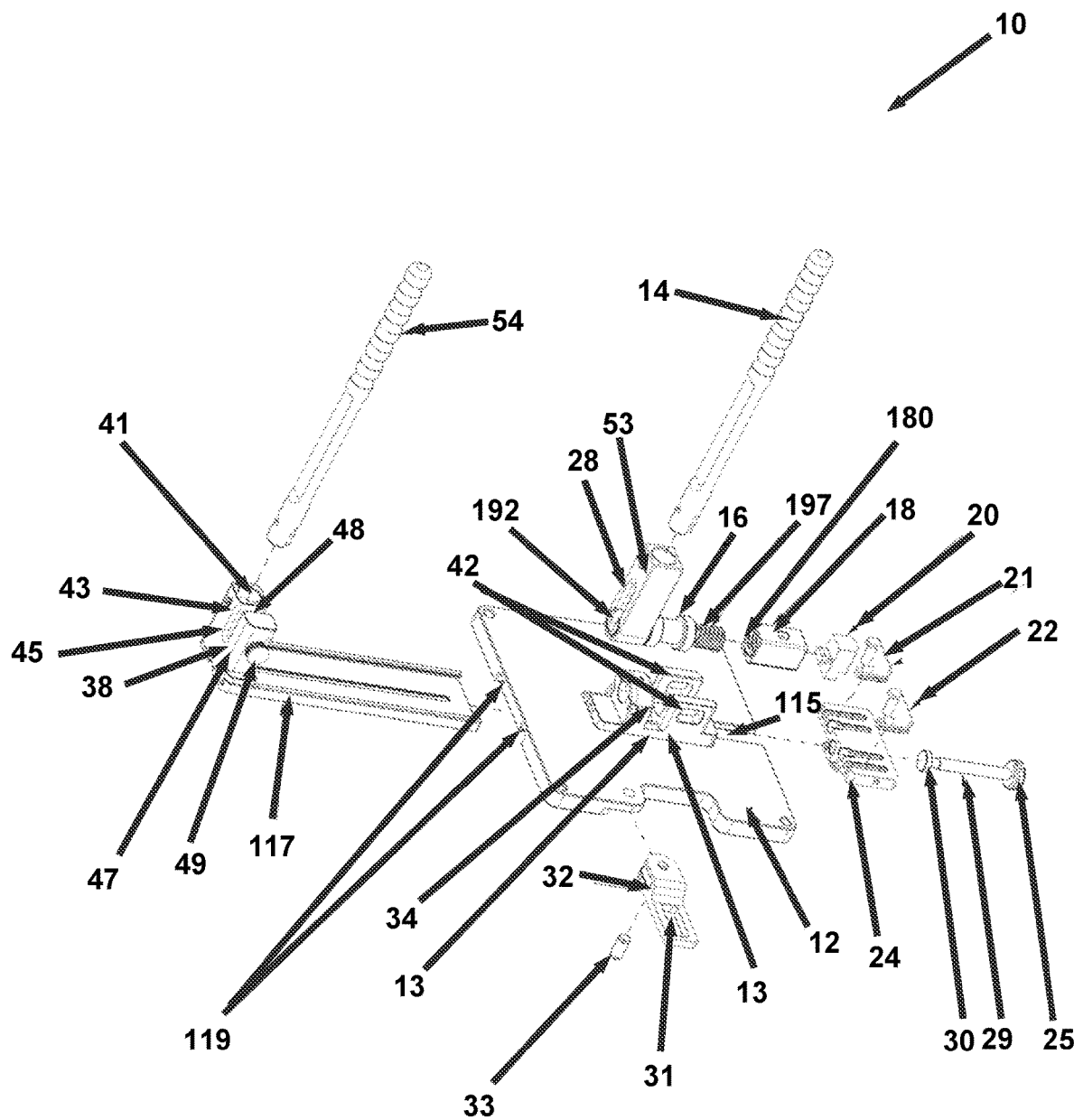
FIG. 1 is an exploded perspective view of the orthopedic implant altering apparatus, e.g., bone plate bender, in accordance with the present invention.

Referring now to FIG. 1, an orthopedic implant altering apparatus, e.g., bone plate bender, of the present invention is generally indicated by the numeral 10. This orthopedic implant altering apparatus 10 can be applied to a wide variety of orthopedic implants, including but not limited to bone plates, intramedullary nails, pins, and rods with alteration, including the steps of both bending (including twisting) and cutting.

A base plate 12 provides a foundation for the entire orthopedic implant altering apparatus 10. Unless stated otherwise, it is assumed the preferred material for the components of this orthopedic implant altering apparatus 10 is metal, but a variety of composite and other types of material may suffice. Either mounted on top of the base plate 12 or an integral aspect thereof is a support frame 13. The support frame 13 can be mounted to the base plate 12 by a series of connectors (not shown). The base plate 12 can be mounted in either a horizontal plane or a vertical plane in the style of a wine press.

Figure 2:
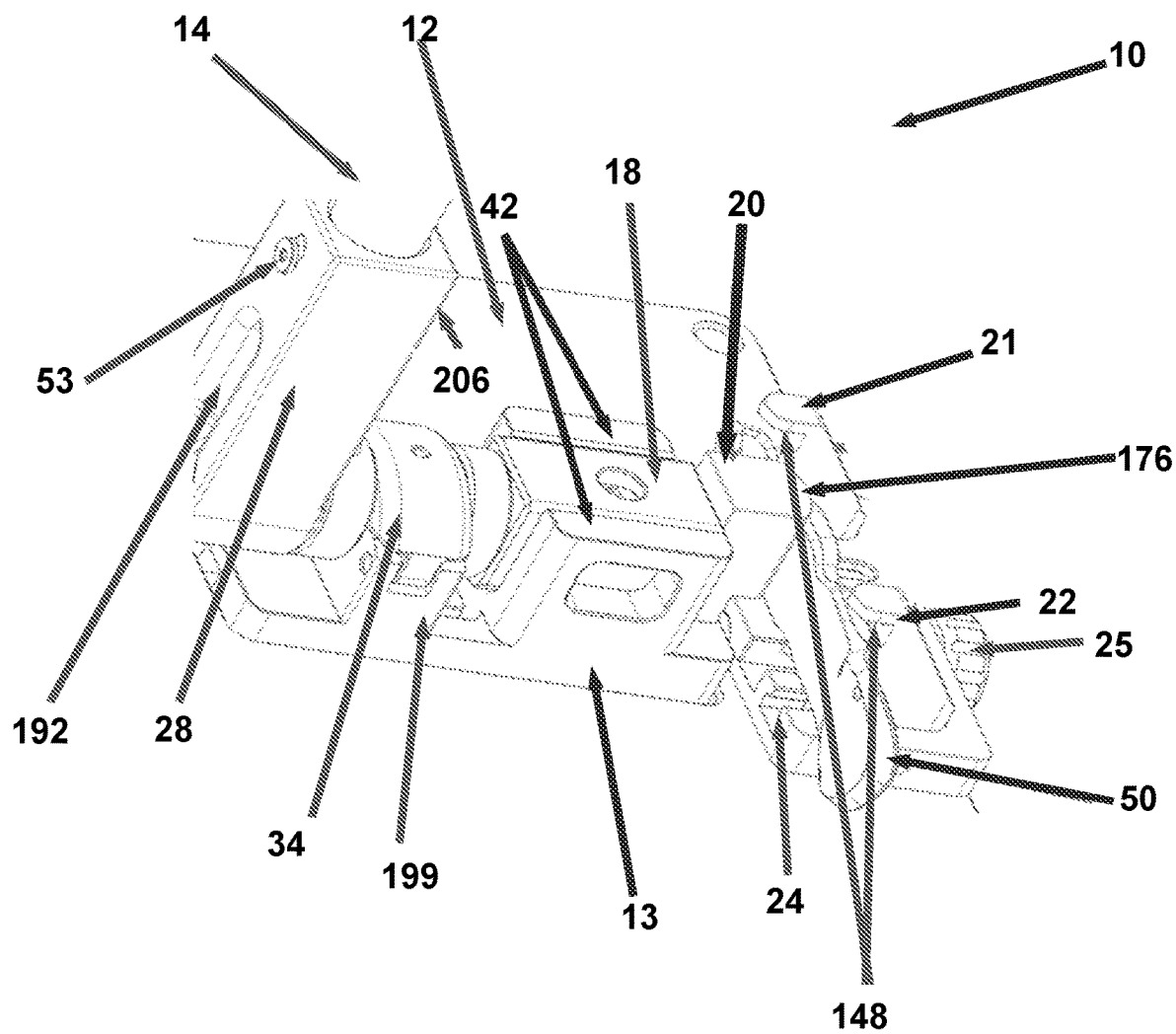
FIG. 2 is an isolated perspective view of the orthopedic implant altering apparatus, e.g., bone plate bender, focusing on an anvil (base member and contact member) and uprights with an orthopedic implant positioned in between with a focus on the altering function in accordance with the present invention.
Figure 3:
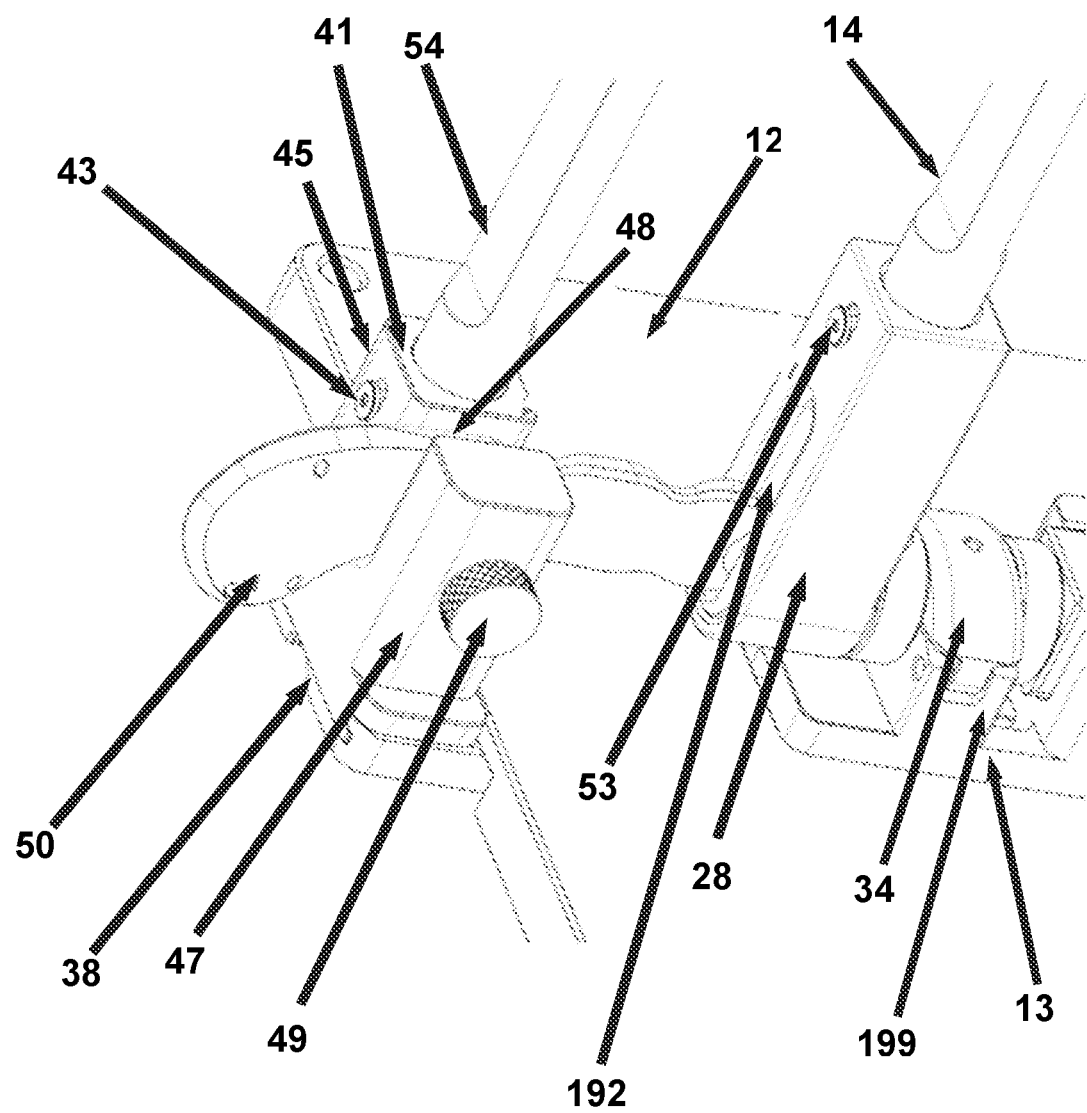
FIG. 3 is an isolated perspective view of the orthopedic implant altering apparatus, e.g., bone plate bender, focusing on a rotatable member having a shaft slot that is attached to a first lever that is aligned with a slot in a movable/translational block having a second lever to provide an axial twist in an orthopedic implant secured between the two slots.
Figure 5:
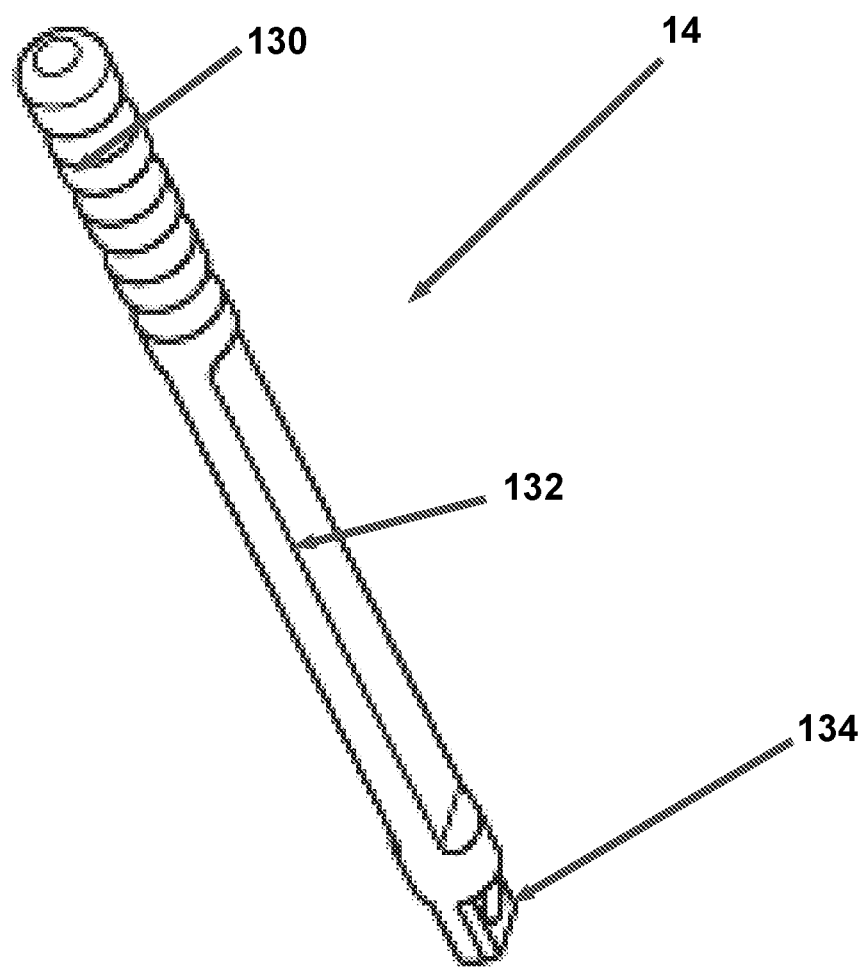
FIG. 5 is an isolated perspective view of a first lever shown in FIG. 1.

Referring now to FIGS. 1-3, there is a first lever 14 that is connected to a first member 28. The first member 28 can be a variety of shapes and sizes. As shown in FIG. 5, the first lever 14 includes a handle 130 that may be collapsible downwards or removable, such as through a threaded sleeve, among numerous other variations. Preferably, this first lever 14 is operated by hand manually. Optionally, there can be indentations 132 in the first lever 14. The first lever 14 is secured within the first member 28. There is an opening 134, as shown in FIG. 10, for attaching a securing mechanism 53, e.g., bolt or screw, shown in FIGS. 1, 2, and 3, for attaching the first lever 14 to the first member 28.

Figure 10:
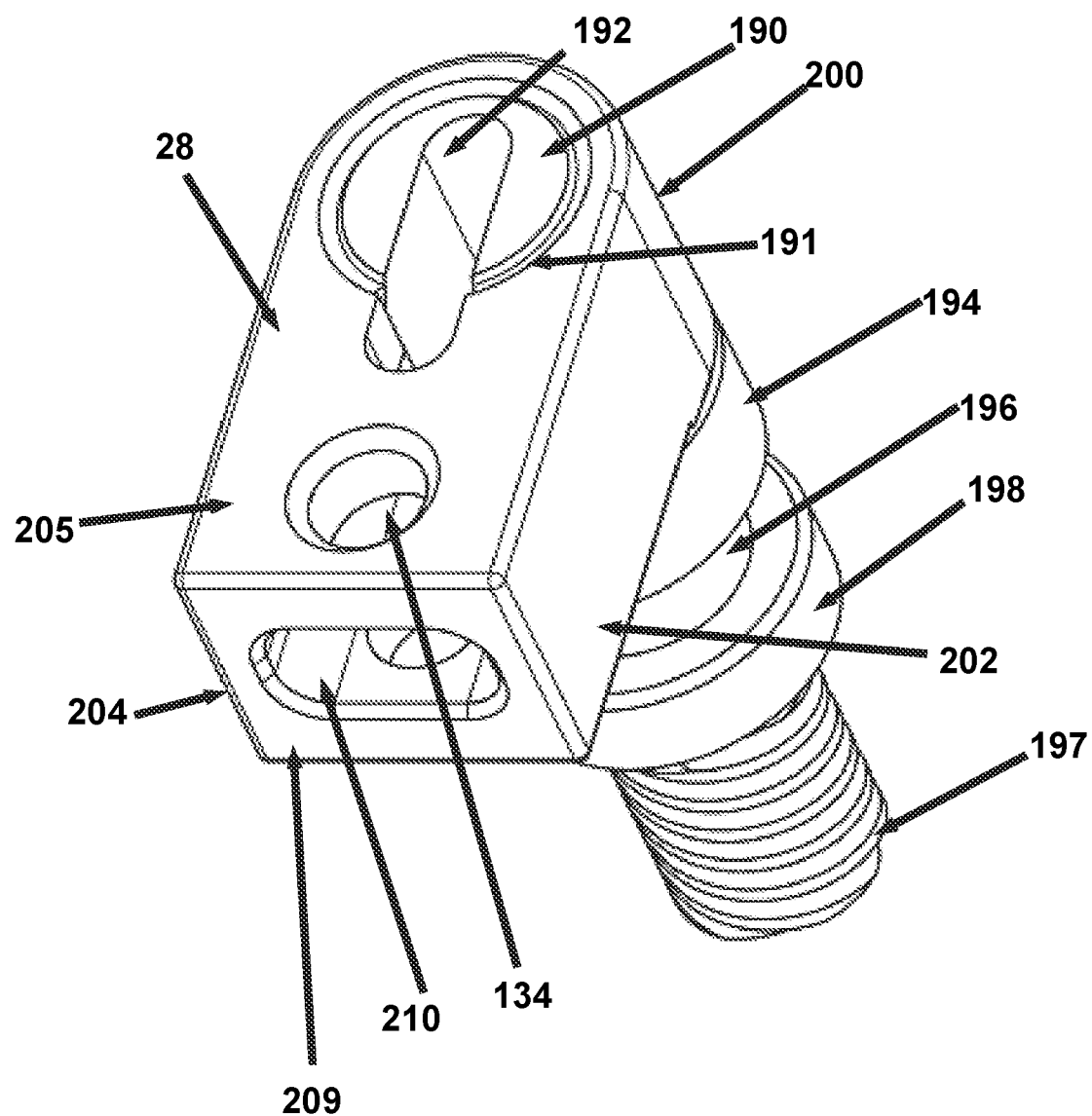
FIG. 10 is a perspective view of a rotatable slotted member that connects the first lever of FIG. 5 with the compound threaded mechanism of FIG. 9.

Referring now to FIG. 10, the first member 28 can be hollow with a first opening slot 192 in a front portion 205 that can receive one end of an orthopedic implant 50, e.g., bone plate, shown in FIGS. 2 and 3. This nonlimiting exemplary embodiment of the first member 28 refers again to FIG. 10, there is a curved bottom portion 200, a first side portion 202, a second side portion 204, and a top portion 209. Within the top portion 209 is an opening 210 for receiving the portion of the first lever 14 that includes the aforementioned opening 134. Opposite the front portion 205 of the first member 28 is a back portion 206, shown in FIG. 2.

Figure 9:
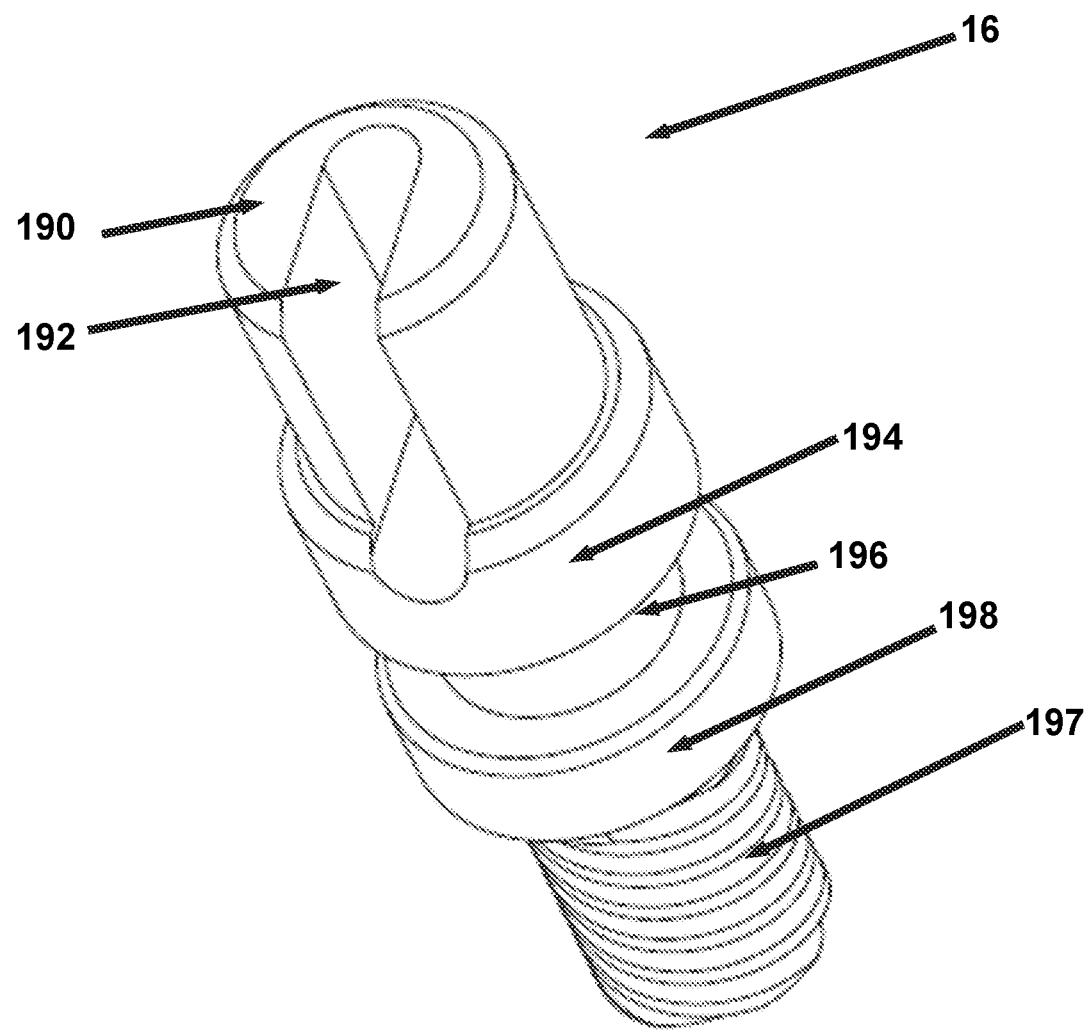
FIG. 9 is an isolated perspective view of a threaded shaft that is activated by the first lever, as shown in FIG. 1.

As shown in FIG. 1, there is a screw mechanism 16 that is attached to the first member 28. A wide variety of screw mechanisms may be feasible with this invention. This can even include a compound coaxial screw type of mechanism. The purpose of this structure is to convert the rotational movement of the first lever 14 to axial movement. Therefore, a wide variety of mechanical mechanisms will suffice. In this nonlimiting embodiment, the screw mechanism 16 is illustrated as being in the form of a threaded shaft. Referring now to FIGS. 9 and 10, the screw mechanism 16 includes a cylindrical member 190 that extends through a cylindrical opening 191 in the first member 28, as specifically shown in FIG. 10. As shown in both FIGS. 9 and 10, within this cylindrical member 190 is a rotatable opening slot 192 for receiving one end of an orthopedic implant 50 to generate an axial twist. In one embodiment, the entire part shown in FIG. 10 is made of two components that have been welded together. There is a first flange member 194 connected between the cylindrical member 190 and a second flange member 196 of a smaller diameter than the first flange member 194. The second flange member 196 is then connected to a third flange member 198 that has a comparable diameter to the first flange member 194. As shown in FIGS. 2 and 3, the second flange member 196 rests in a pair of u-shaped support members 199 that are either attached or integral with the support frame 13. Referring again to FIGS. 9 and 10, the first flange member 194 and the third flange member 198 provide translational constraint for the second flange member 196. There is a threaded member 197 attached to the back end portion of the third flange member 198. There is a top cover 34 that encloses the first flange member 194, the second flange member 196, and the third flange member 198 and securely interconnects with the support frame 13 to prevent any human interaction or contamination with this moving component, which is shown in FIGS. 1, 2 and 3.

Figure 8:
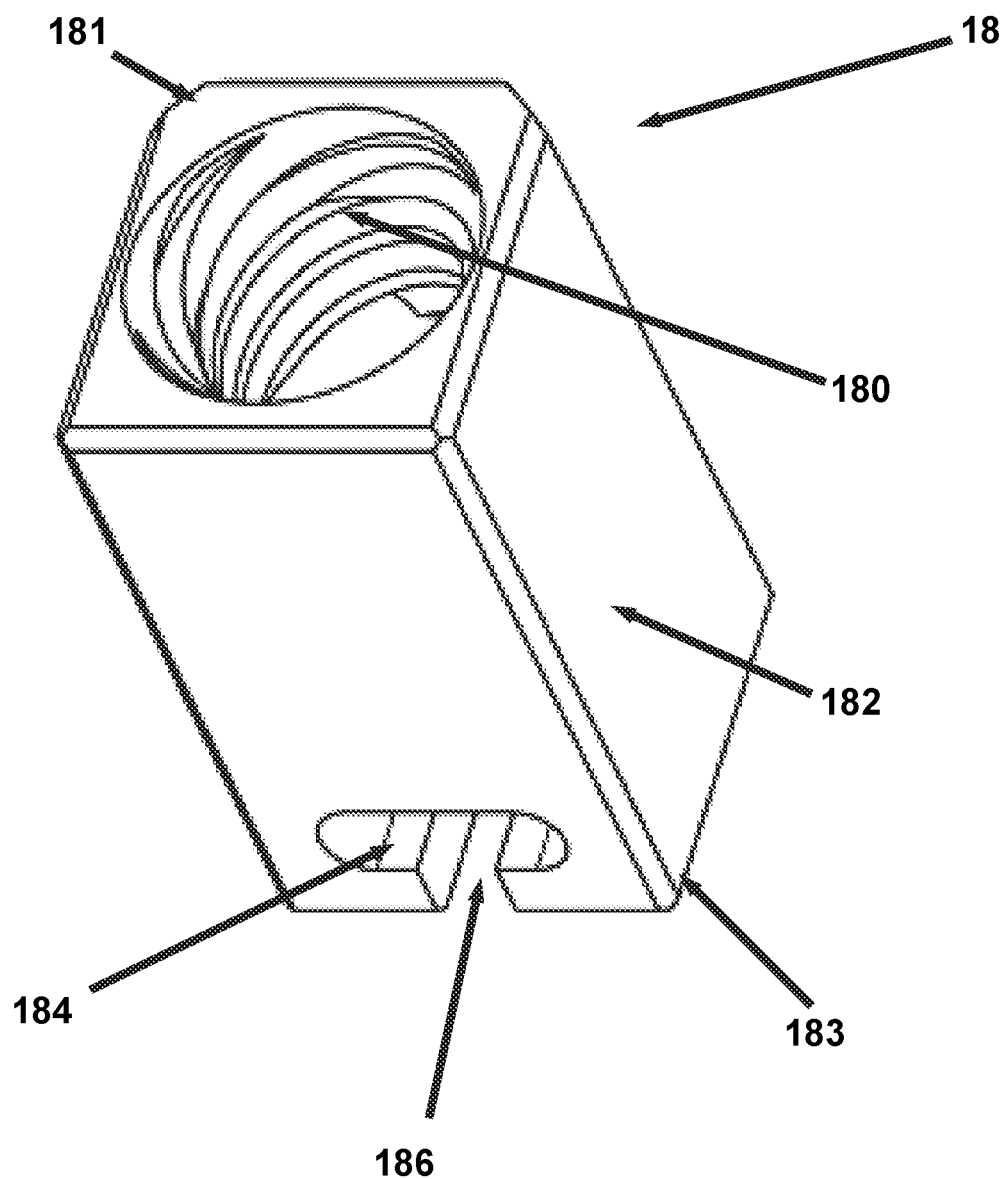
FIG. 8 is an isolated perspective view of an anvil base member that includes a compound threaded mechanism that is interconnected with the threaded shaft of FIG. 9 for providing axial movement of the anvil contact member of FIG. 7.

A type of contact device for bending or cutting the orthopedic implant is an anvil. In this particular illustrative, but nonlimiting, embodiment, the anvil is broken down into two components: an anvil base member 18 and an anvil contact member 20. The anvil, however, can be a unitary structure or more than two components. As shown in FIGS. 1 and 8, the threaded member 197 of the screw mechanism 16 engages a threaded opening 180 located in a first end portion 181 of the anvil base member 18 that provides conversion of the rotational motion of the first lever 14 into axial movement of the anvil base member 18. The anvil base member 18 is mounted on the support frame 13 between dual securing members 42 that, cradles and supports anvil base member 18. Axial movement of the anvil base member 18 can be extensive and can reach up to fifteen millimeters or more.

Referring now to FIG. 8, the anvil base member 18 can be a variety of shapes and sizes and can have a rectangular body 182. There is a second end portion 183 of the anvil base member 18 that preferably includes an opening 184 having a t-shaped slot 186.

There are a wide variety of bending and cutting tools that can be interchangeably inserted and removed from the cylindrical opening 184 and slot 186 in the second end portion 183 of the anvil base member 18. For the purposes of this invention, these bending and cutting tools will be generally referred to as an anvil, but punches and comparable types of bending and cutting implements can also be utilized and completely interchanged.

Figure 7:
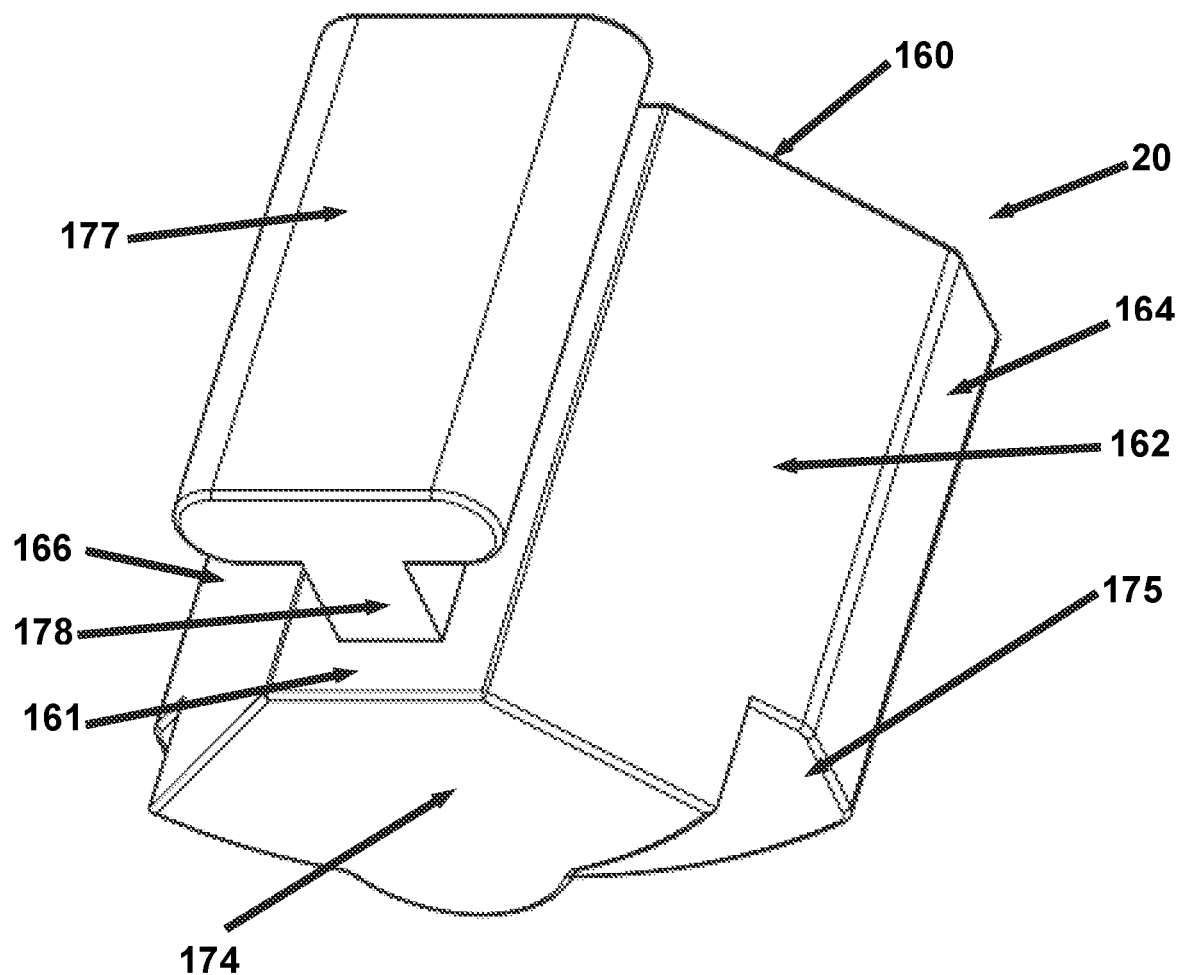
FIG. 7 is an isolated perspective view of an anvil contact member, as shown in FIG. 1.

An illustrative, but nonlimiting example, of an anvil contact member includes a medium anvil most suited for bending bone plates that is generally indicated by the numeral 20, as shown in FIG. 7. There is an attachment member 177 connected to a perpendicular attachment member 178 (together forming a t-shaped attachment member) that can slide into the opening 184 with associated slot 186 of the anvil base member 18. A nonlimiting shape of the anvil contact member 20 includes a top portion 160, a first side portion 161 attached to the perpendicular attachment member 178, a second side portion 162, a third side portion 164, a fourth side portion 166, a main bottom portion 174 and a raised secondary bottom portion 175. The secondary bottom portion 175 is important in that its purpose is to secure the plate in its place to prevent the plate from "popping" out of position due to the large force necessary especially for bending the plate on the flat (e.g., coronal bend of the plate). The front portion of the anvil contact member 176 is shown in FIG. 2.

Figure 11:
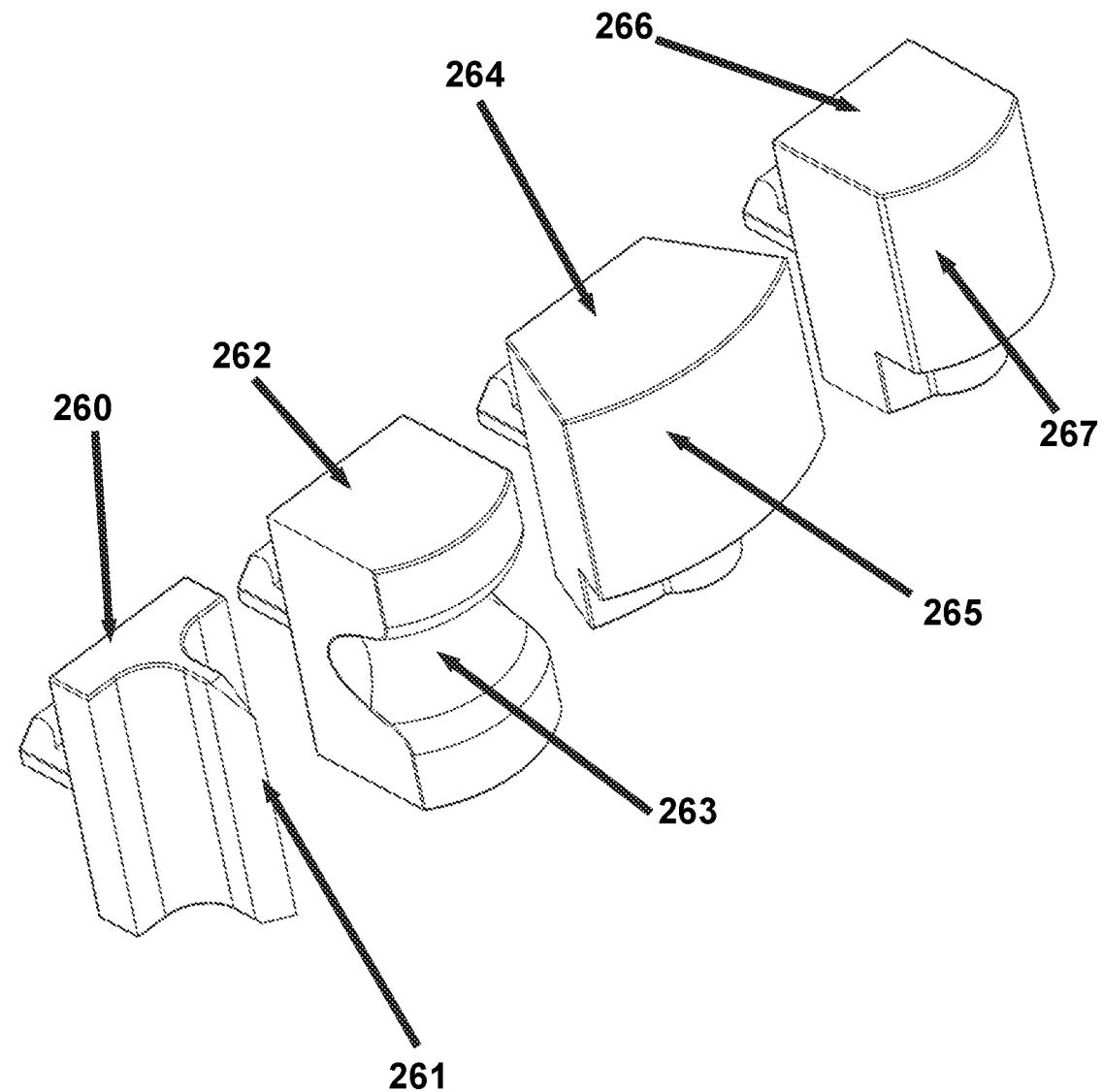
FIG. 11 is a perspective view of an illustrative, but nonlimiting, series of interchangeable anvils and cutters associated with the present invention.

The anvil contact member 20 can be concave or convex to administer any type of orthopedic implant alteration desired, from bending to cutting. Referring now to FIG. 11, this can include a rod cutter 260 having cutting edge 261, a rod bender 262 having a curved and recessed bending surface 263 for securely receiving a rod, a broad bender 264 with a wide bending surface 265, and a narrow bender 266 with a narrow bending surface 267 among numerous other types and permutations of both cutting and bending implements. All of these components are preferably completely interchangeable.

The axial force of the anvil contact member 20 is applied to the orthopedic implant 50, such as a bone plate. There is preferably, but not necessarily, a first upright post 21 and a second upright post 22 positioned on the other side of the orthopedic implant 50 to apply pressure so the axial movement of the anvil contact member 20 can alter the shape or even physically cut the orthopedic implant 50. There are a wide variety of upright posts 21, 22 that can be used in conjunction with an anvil contact member 20. Two or more upright posts 21, 22 are preferred so that the anvil contact member 20 can bend or cut the orthopedic implant 50 at points located between the impact of the anvil contact member 20 and the upright posts 21, 22. The upright posts 21, 22 can take a myriad of shapes with the common element as typically, but not necessarily, a contact portion 148 having a generally cylindrical shape, as shown in FIG. 2. However, these upright posts 21, 22 can be either concave or convex and are entirely interchangeable. The linear travel of the anvil contact member 20 can be extensive, preferably at least fifteen millimeters or greater.

Figure 4:
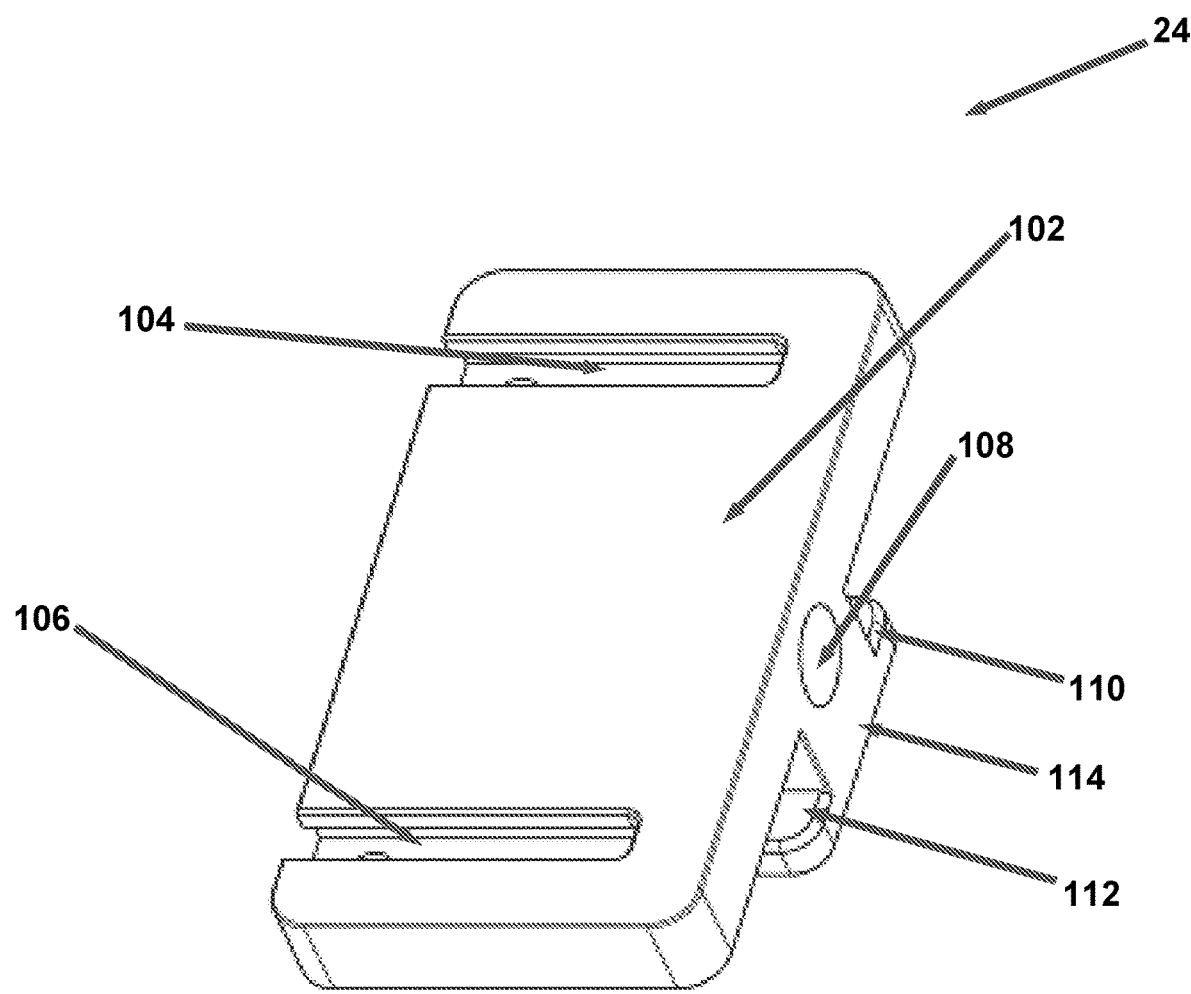
FIG. 4 is an isolated perspective view of an adjustable table, which permits the precise positioning of upright posts, as shown in FIG. 1.

Referring to FIG. 1 and specifically FIG. 4, there is an adjustable table 24 that has a top plate 102 with a first T-shaped receiving groove 104 for receiving a prong (not shown) of the first upright post 21 and a second T-shaped receiving groove 106 for receiving a prong (not shown) of the second upright post 22. In addition, there is a threaded opening 108 for receiving an adjustment knob 25, shown in FIG. 1. The adjustment knob 25 has a threaded rod 29 attached thereto that has a cap 30 mounted on the end to provide fine positioning, adjustment, and tightening of the adjustable table 24 as shown in FIG. 1 in relation to the base plate 12.

Referring again to FIG. 4, there is a t-shaped lower support member 114 that has a first support member 110 and a second support member 112 that form the guiding structure for the adjustable table 24. The first support member 110 and a second support member 112 engage slot 115, located at the bottom of the base plate 12, as shown in FIG. 1.

Therefore, as shown in FIG. 2, by applying rotational motion to the first lever 14, this is converted through the screw mechanism, e.g., threaded shaft, 16 to axial motion that moves an anvil contact member 20 against an orthopedic implant 50 that is rigidly positioned against two upright posts 21,22 that are mounted on the movable and adjustable table 24 to alter the orthopedic implant 50 by either bending or cutting the orthopedic implant 50. The first lever 14 can be either pulled or pushed depending on the orientation of the orthopedic implant altering apparatus 10 until a desired bend or cut in the orthopedic implant 50 is achieved. If additional bends are required in the orthopedic implant, e.g., bone plate 30, then the anvil contact member 20 and the orthopedic implant, e.g., bone plate, 50 can be adjusted accordingly.

The second major function of the present invention is to create an axial twist in the orthopedic implant 50. A second lever 54 is shown in the illustrative embodiment as identical to the first lever 14 but does not necessarily need to be that similar. Referring now to FIGS. 1 and 3, this second lever 54 is connected to and inserted into a second member 38 through opening 41 and secured within. As with the first lever 14 in FIG. 5, the second lever 54 in FIG. 6 includes a handle 130, that may be collapsible downwards, such as through a threaded sleeve, among numerous other variations, Preferably, this second lever 54 is operated by hand manually. Optionally, there can be indentations 132 in the second lever 54.

Figure 6:
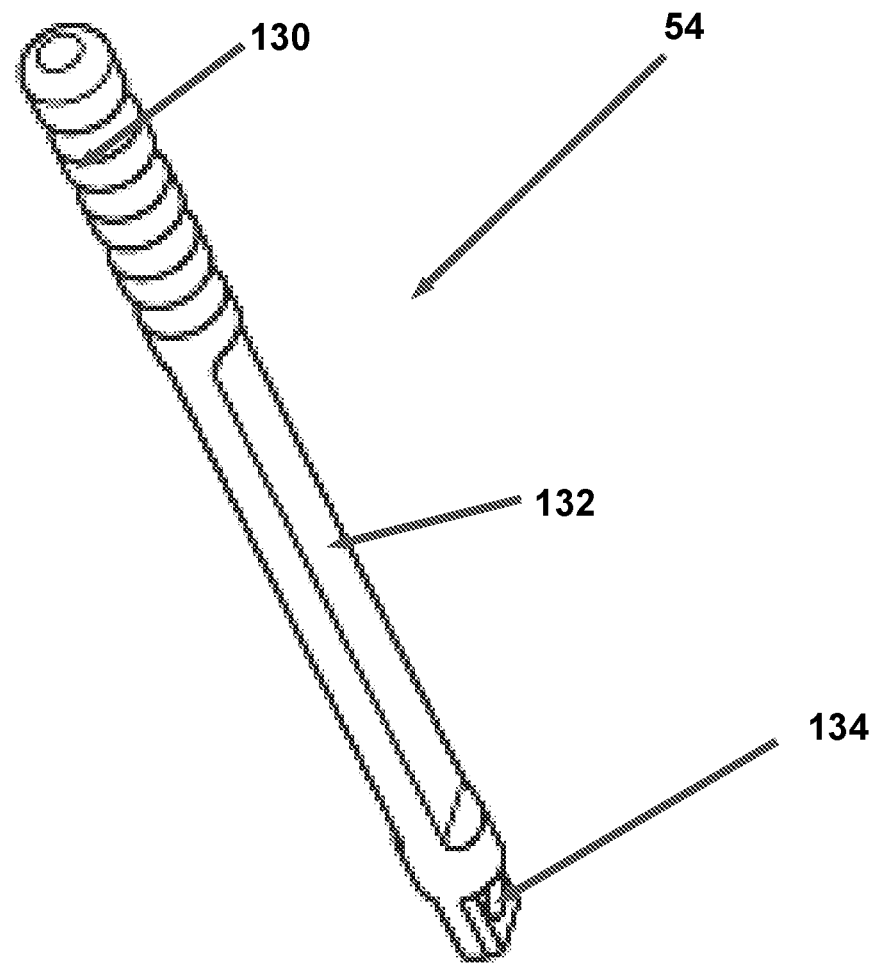
FIG. 6 is an isolated perspective view of a second lever shown in FIG. 1.

There is an opening 134 in the second lever 54 shown in FIG. 6 for attaching a securing mechanism 43, e.g., bolt or screw shown in FIGS. 1 and 3, for attaching the second lever 54 to the second member 38. The second member 38 can be a variety of shapes and sizes but is preferably u-shaped with a first upward prong 45 that secures the second lever 54. The second upright prong 47 is spaced from the first upright prong 45 to provide a second opening slot 48 in the second member 38. As shown, this second opening slot 48 is fixed and is not rotatable like slot 192 in the first member 28 although in a different embodiment, the slot 48 can be made as a rotatable component.

There is an adjustment knob 49 attached to a screw and cap (not shown) that is comparable to the adjustment knob 25 that provides fine positioning of the adjustable table 24. The knob 49 as shown is a spring-loaded plunger although a threaded knob would also be acceptable. This adjustment knob 49 can apply pressure to secure an orthopedic implant 50 in this second member 38 within the second slot 48. Therefore, the orthopedic implant 50 can be placed between the aforementioned rotational first opening slot 192 in the first member 28 and this fixed second opening slot 48 in the second member 38 and is aligned therewith. By securing the second end of the orthopedic implant 50 with the adjustment knob 49 in this second member 38 and applying rotational force to the first lever 14 with the rotational first opening slot 192, then axial twist can be applied to the orthopedic implant 50. The distance between the first opening slot 192 and the second opening slot 48 can determine the length of the twist. This is especially effective when the orthopedic implant 50 is a bone plate so that the bone plate can conform to curvatures in a patient's skeletal system. The second lever 53 can be either pulled or pushed depending on the orientation of the orthopedic implant altering apparatus 10 until a desired axial twist in the orthopedic implant 50 is achieved.

This second member 38 is movable in relation to the base plate 12 to adjust to the length of the twist of the orthopedic implant 50 and aligned therewith so that orthopedic implants 50 of various lengths can be placed between the rotational first opening slot 192 in the first member 28 and this fixed second opening slot 48 in the second member 38.

One illustrative but nonlimiting mechanism for moving the second member 38 includes a track with two outer upwardly projecting prongs 117 with two downward projecting slots 119 in the underside of the base member 12. However, there are a myriad of ways of moving this second member 38 in relation to the first member 28.

When gripped, this second lever 54 can counteract the torque applied to the base plate 12 to prevent movement. Optionally, as shown in FIG. 1, a stabilizing member 32, having a slot 31, can be attached to the base plate 12 with a pin 33 for attaching the stabilizing member 32 to the base plate 12 to provide additional stabilization and support of the entire orthopedic implant altering apparatus, e.g., bone plate bender, 10 by essentially expanding the size of the base plate 12 and also expanding the surface area in the plane that torque is applied to limit the flipping or lifting of the base plate.

Figure 12:
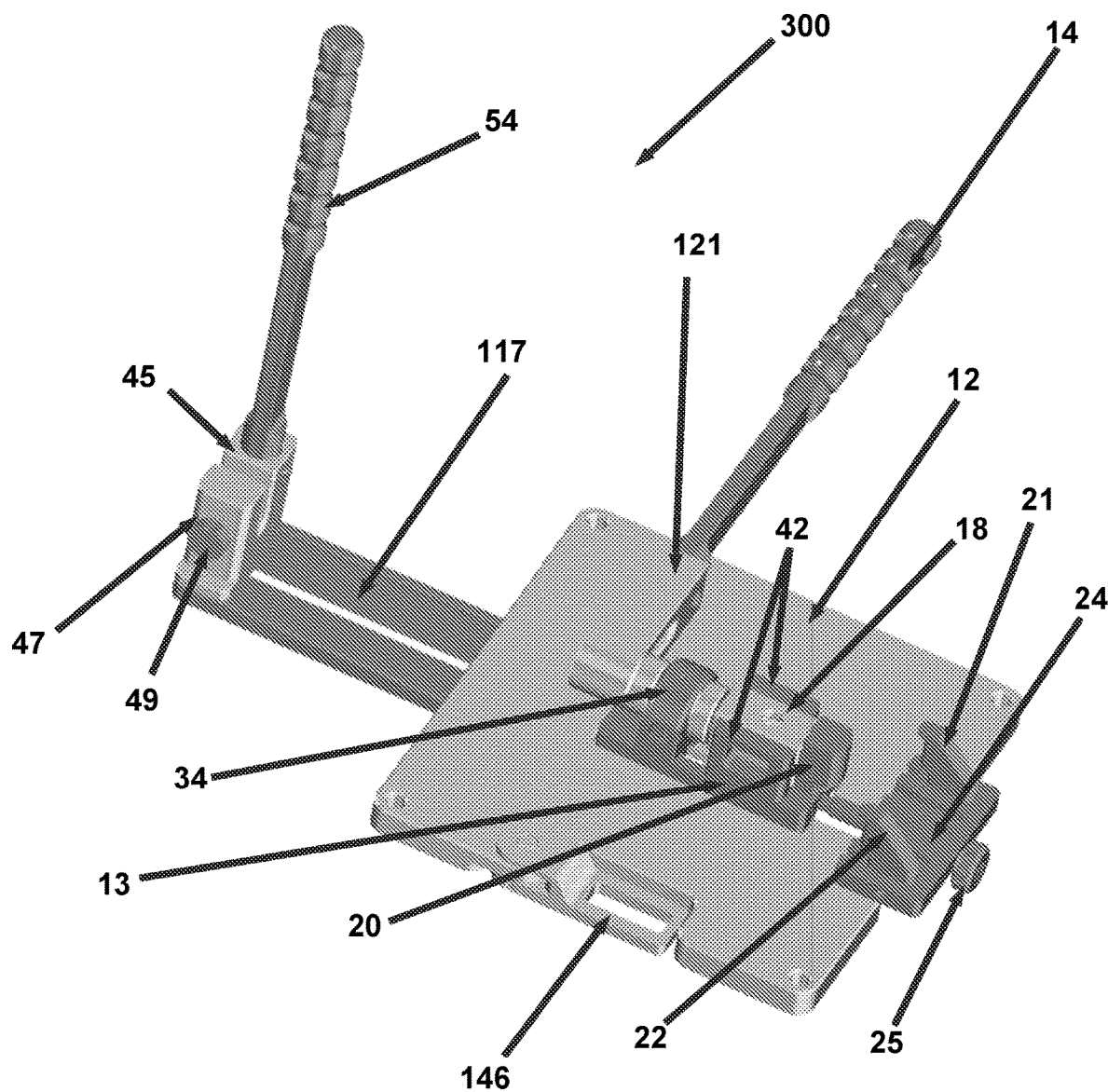
FIG. 12 is a perspective view of an alternative embodiment of FIG. 1 of an implant altering apparatus, e.g., bone plate bender, where the only differences include a cover over the first lever to prevent contamination, provide ease of cleaning, as well as a securing mechanism for the base plate.

A preferred embodiment shown in FIG. 12 and generally indicated by the numeral 300 is very similar to this prior embodiment described above with the sole exception of a cover 121 that keeps the connection of the first lever 14 and the screw mechanism 15 covered for operational safety as well as sanitation and ease of clean up. An additional stabilization mechanism 146 provides a slot for securing the base plate 12 to a surface with an adjustable bolt or screw (not shown) that can engage the slot so that the entire orthopedic implant system 300 is stationary and secure.

From the foregoing, it can be seen that the present disclosure accomplishes at least all of the stated objectives.

LIST OF REFERENCE CHARACTERS

The following table of reference characters and descriptors are not exhaustive, nor limiting, and include reasonable equivalents. If possible, elements identified by a reference character below and/or those elements which are near ubiquitous within the art can replace or supplement any element identified by another reference character.

TABLE 1

List of Reference Characters

| | |
|---|---|
| 10 | Orthopedic Implant Altering Apparatus; e.g., bone plate bender |
| 12 | Base plate |
| 13 | Support frame |
| 14 | First lever |
| 16 | Screw mechanism, e.g., threaded shaft |
| 18 | Anvil base member |
| 20 | Anvil contact member |
| 21 | First upright post |
| 22 | Second upright posts |
| 24 | Adjustable table |
| 25 | Adjustment knob |
| 28 | First member |
| 29 | Threaded rod |
| 30 | Cap |
| 31 | Slot |
| 32 | Stabilizing member |
| 33 | Pin for attaching stabilizing member to the base plate |
| 34 | Top cover |
| 38 | Second member |
| 41 | Opening in the second member |
| 42 | Dual securing members for anvil base member |
| 43 | Securing mechanism, e.g., screw or bolt |
| 45 | First upward prong |
| 47 | Second upward prong |
| 48 | Fixed opening slot between the first and second upward prongs of the second member for the orthopedic implant |
| 49 | Adjustable knob for the second member |
| 50 | Orthopedic implant, e.g., bone plate |
| 53 | Securing mechanism, e.g., screw or bolt |
| 54 | Second lever |
| 102 | Top plate of adjustable table |
| 104 | First T-shaped receiving groove for a prong of the first upright post |
| 106 | Second T-shaped receiving groove for a prong of the second upright post |
| 108 | Threaded opening for an adjustment knob |
| 110 | First support member for movable anvil base |
| 112 | Second support member for movable anvil base |
| 114 | T-shaped lower support member for movable anvil base |
| 115 | Slot in the base plate |
| 117 | Track with two outer upwardly projecting prongs |
| 119 | Slots that are downward projecting and located on the bottom of the base plate |
| 121 | Cover |
| 130 | Handle of a lever (first or second) |
| 132 | Indentations of a lever (first or second) |
| 134 | Opening for attaching a securing mechanism, e.g., bolt or screw |
| 146 | Stabilization mechanism |
| 148 | Contact portion of upright posts |
| 160 | Top portion of the anvil contact member |
| 161 | First side portion of the anvil contact member |
| 162 | Second side portion of the anvil contact member |
| 164 | Third side portion of the anvil contact member |
| 166 | Fourth side portion of the anvil contact member |
| 174 | Main bottom portion of the anvil contact member |
| 175 | Raised secondary bottom portion of the anvil contact member |
| 176 | Front of anvil contact member |
| 177 | Cylindrical attachment member |
| 178 | Perpendicular attachment member |
| 180 | Threaded opening |
| 181 | First end portion of an anvil base member |
| 182 | Rectangular body of anvil base member |
| 183 | Second end portion of anvil base member |
| 184 | Cylindrical opening in anvil base member for attaching an anvil |

TABLE 1-continued

List of Reference Characters contact member
186 Slot in the cylindrical opening of the anvil base member for attaching an anvil contact member
190 Cylindrical rotatable member
191 Cylindrical opening in the first member
192 Rotatable opening slot for orthopedic implant
194 First flange member
196 Second flange member
197 Threaded member
198 Third flange member
199 Pair of u-shaped support members
200 Curved bottom portion of the first member
202 First side portion of the first member
204 Second side portion of the first member
205 Front portion of the first member
206 Back portion of the first member
209 Top portion of the first member
210 Opening in the bottom portion of the first member
260 Rod cutter
261 Cutting edge
262 Rod bender
263 Curved bending surface
264 Broad bender
265 Wide bending surface
266 Narrow bender
267 Narrow bending surface
300 Alternative preferred embodiment of the present invention Glossary Unless defined otherwise, all technical and scientific terms used above have the same meaning as commonly understood by one of ordinary skill in the art to which embodiments of the present disclosure pertain.

The terms "a," "an," and "the" include both singular and plural referents.

The term "or" is synonymous with "and/or" and means any one member or combination of members of a particular list.

As used herein, the term "exemplary" refers to an example, an instance, or an illustration, and does not indicate a most preferred embodiment unless otherwise stated.

The term "about" as used herein refers to slight variations in numerical quantities with respect to any quantifiable variable. Inadvertent error can occur, for example, through use of typical measuring techniques or equipment or from differences in the manufacture, source, or purity of components.

The term "substantially" refers to a great or significant extent. "Substantially" can thus refer to a plurality, majority, and/or a supermajority of said quantifiable variables, given proper context.

The term "generally" encompasses both "about" and "substantially."

The term "configured" describes structure capable of performing a task or adopting a particular configuration. The term "configured" can be used interchangeably with other similar phrases, such as constructed, arranged, adapted, manufactured, and the like.

Terms characterizing sequential order, a position, and/or an orientation are not limiting and are only referenced according to the views presented.

The "invention" is not intended to refer to any single embodiment of the particular invention but encompasses all possible embodiments as described in the specification and the claims. The "scope" of the present disclosure is defined by the appended claims, along with the full scope of equivalents to which such claims are entitled. The scope of the disclosure is further qualified as including any possible modification to any of the aspects and/or embodiments disclosed herein which would result in other embodiments, combinations, subcombinations, or the like that would be obvious to those skilled in the art.

What is claimed is:

1. An orthopedic implant altering apparatus, comprising:
a base plate having a support member;
a first lever;
a first member that is connected to the first lever, the first member being supported and rotatable in the support member;
a screw mechanism, having a first end portion and a second end portion, wherein the first end portion is connected to the first member;
an anvil, having a first end portion and a second end portion, wherein the first end portion is connected to the second end portion of the screw mechanism to translate rotational force from the first lever into an axial force;
a movable table; and
a plurality of upright posts attached to the movable table, wherein an orthopedic implant positioned between the anvil and the plurality of upright posts can be altered by applying force through axial movement of the anvil.

2. The orthopedic implant altering apparatus according to claim 1, wherein the screw mechanism includes a first end portion attached to the first member and the second end portion having a threaded shaft, wherein the anvil includes an anvil contact member and an anvil base member having a first end portion with recessed threads that interact with the threaded shaft of the screw mechanism and a second end portion of the anvil base member that can selectively connect to the anvil contact member.

3. The orthopedic implant altering apparatus according to claim 1, wherein the orthopedic implant is selected from the group consisting of a bone plate, intramedullary nails, pins, and rods.

4. The orthopedic implant altering apparatus according to claim 1, wherein the base plate can be located in a vertical plane.

5. The orthopedic implant altering apparatus according to claim 1, further comprising a second lever attached to a second member having a fixed slot, wherein the second member is adjustably movable along the base plate, and the first member also includes a rotatable slot that is rotatable by the first lever; wherein the orthopedic implant can be selectively placed between the slot of the first member and the slot of the second member with the first lever being able to rotate the slot of the first member and apply an axial twist to an orthopedic implant.

6. The orthopedic implant altering apparatus according to claim 5, wherein the second member includes a sliding mechanism that engages the base plate allowing movement of the second member so that a distance between the rotatable slot of the first member and the fixed slot of the second member can secure the orthopedic implant and the second member also includes an adjustable securing mechanism for fixedly securing the orthopedic implant within the fixed slot of the second member.

7. The orthopedic implant altering apparatus according to claim 1, wherein the movable table has at least one protruding flange member that engages an underside portion of the base plate.

8. The orthopedic implant altering apparatus according to claim 1, wherein each upright post of the plurality of upright posts can vary based on the orthopedic implant and desired alteration and is selectively interchangeable with the movable table.

9. The orthopedic implant altering apparatus according to claim 8, wherein each upright post of the plurality of upright posts is selectively engageable with at least one slot in the movable table.

10. The orthopedic implant altering apparatus according to claim 1, further comprising a threaded opening within the movable table and an adjustment knob inserted within the threaded opening to be able to manually adjust a position of the plurality of upright posts in relation to the anvil so that an orthopedic implant is securely positioned in between.

11. The orthopedic implant altering apparatus according to claim 5, wherein the second lever when gripped can counteract torque produced by the first lever in either a bending or twisting operation to secure the base plate's position.

12. The orthopedic implant altering apparatus according to claim 2, wherein the anvil contact member can be in the form of the group consisting of a medium bender, a narrow bender, a broad bender, a rod bender, and a rod cutter and is selectively interchangeable with the anvil base member depending on a patient and associated medical condition.

13. The orthopedic implant altering apparatus according to claim 2, wherein the anvil base member includes an opening, and the anvil contact member includes an attachment member that is securely received within the opening of the anvil base member.

14. The orthopedic implant altering apparatus according to claim 5, wherein the first lever is located underneath a cover and the second lever is attached to a track that is received underneath the base plate and is adjustably movable.

15. An orthopedic implant altering apparatus, comprising:
a base plate having a support member;
a first lever;
a first member that is connected to the first lever, the first member being supported and rotatable in the support member and having a rotatable slot;
a threaded shaft, having a first end portion and a second end portion, wherein the first end portion is connected to the first member;
an anvil base member, having a first end portion and a second end portion, wherein the first end portion is a threaded portion and interacts with the second end portion of the threaded shaft to translate rotational force from the first lever into an axial force and the second end portion of the anvil base member includes an opening;
an anvil contact member attached to the anvil base member through an attachment member that is received by the opening of the anvil base member;
a plurality of upright posts attached to a movable table;
wherein an orthopedic implant positioned between the anvil contact member and the plurality of upright posts can be altered by applying force through axial movement of the anvil contact member; and
a second lever attached to a second member having a fixed slot that is adjustably movable along the base plate and the second member includes an adjustable securing mechanism for fixedly securing the orthopedic implant in the fixed slot, wherein the orthopedic implant can be selectively placed between the rotatable slot of the first member and the fixed slot of the second member, with the first lever being able to apply an axial twist to the orthopedic implant.

16. The orthopedic implant altering apparatus according to claim 15, wherein the orthopedic implant is selected from the group consisting of bone plates, intramedullary nails, pins, and rods.

17. The orthopedic implant altering apparatus according to claim 15, wherein the anvil contact member is selectively attachable to the anvil base member and the upright posts are selectively attachable to the movable table, wherein both the anvil contact member and upright posts can vary depending on the orthopedic implant and medical condition of the patient.

18. The orthopedic implant altering apparatus according to claim 15, wherein the movable table includes a protruding flange member that engages the underside of the base plate, and there is a threaded opening within the movable table and an adjustment knob inserted within the threaded opening to be able to manually adjust the position of the plurality of upright posts in relation to the anvil contact member so that an orthopedic implant can be securely positioned in between the anvil contact member and the upright posts.

19. A method for altering orthopedic implants, comprising:
inserting an orthopedic implant securely between an anvil and a plurality of movable upright posts; and
rotating a first lever having a first member that is supported and rotatable in a support member that is attached to a base plate, wherein a first end portion of the first member is connected to a screw mechanism that is then connected to the anvil,
wherein rotational force of the first lever is converted to axial movement to alter the orthopedic implant due to force caused by the anvil against the orthopedic member that is pressed against the plurality of upright posts mounted on a movable table.

20. The method for altering orthopedic implants according to claim 19, further comprising:
placing and securing an orthopedic implant in a fixed slot in a second member and a rotatable slot in the first member; and
rotating the first lever to apply an axial twist to the orthopedic implant.

* * * * *